United States Patent [19]

Zeng

[11] Patent Number: 5,525,471

[45] Date of Patent: Jun. 11, 1996

[54] ENZYMATIC DEGRADING SUBTRACTION HYBRIDIZATION

[75] Inventor: Jin Zeng, Rockville, Md.

[73] Assignee: The United States of America as represented by the Secretary of the Department of Health and Human Services, Washington, D.C.

[21] Appl. No.: 322,075

[22] Filed: Oct. 12, 1994

[51] Int. Cl.6 .................................................. C12Q 1/68
[52] U.S. Cl. ............................................ 435/6; 435/91.2
[58] Field of Search ...................................... 435/6, 91.2

[56] References Cited

PUBLICATIONS

Gibco BRL Catalogue (1992) p. 271.
The Stratagene Catalog (1988) p. 39.
Zing et al. (1994) Nucleic Acids Research 22(21):pp. 4381–4385.
Cecchini, et al., "Identification of Genes Up–Regulated in Dedifferentiating *Nicotania glauca* Pith Tissue, Using an Improved Method for Constructing a Subtractive cDNA Library", *Nucleic Acids Research*, 21:24:5742–5747, 1993.
Davis, et al., "Expression of a Single Transfected cDNA Converts Fibroblasts to Myoblasts", *Cell*, 51:987–1000, 1987.
Duguid, et al., "Library Subtraction of In Vitro cDNA Libraries to Identify Differentially Expressed Genes in Scrapie Infection", *Nucleic Acids Research*, 18:9:2789–2792, 1989.
Hedrick, et al., "Isolation of cDNA Clones Encoding T Cell–Specific Membrane–Associated Proteins", *Nature*, 308:8:149–153, 1984.
Kaufman, et al., "Restriction Endonuclease Cleavage at the Termini of PCR Products", 9:3:304–306, 1990.
Kohne, et al., "Room Temperature Method for Increasing the Rate of DNA Reassociation by Many Thousandfold: The Phenol Emulsion Reassociation Technique", *Biochemistry*, 16:24:5329–5341, 1977.

Lebeau, et al., "PCR Driven DNA–DNA Competitive Hybridization: A New Method for Sensitive Differential Cloning", *Nucleic Acids Research*, 19:17:4778, 1991.
Liang, et al., "Differential Display of Eukaryotic Messenger RNA by Means of The Polymerase Chain Reaction", *Science*, 257:967–971, 1992.
Liang, et al., "Distribution and Cloning of Eukaryotic mRNAs by Means of Differential Display: Refinements and Optimization", *Nucleic Acids Research*, 21:14:3269–3275, 1993.
Lisitsyn, et al., "Cloning the Differences Between Two Complex Genomes", *Science*, 259: 946–951, 1993.
Putney, et al., "A DNA Fragment With an α–Phosphorothioate Nucleotide At One End is Asymmetrically Blocked From Digestion by Exonuclease III and Can Be Replicated In Vitro. *Proc. Natl. Acad. Sci. USA*", 78:12:7350–7354, 1981.
Sargent, et al., "Differential Gene Expression In The Gastrula of *Xenopus laevis*", *Science*, 222:135–139, 1983.
Sive, et al., "A Simple Subtractive Hybridization Technique Employing Photoactivatable Biotin and Phenol Extraction", *Nucleic Acids Research*, 16:22:10937, 1988.

(List continued on next page.)

*Primary Examiner*—W. Gary Jones
*Assistant Examiner*—Ethan Whisenant
*Attorney, Agent, or Firm*—Knobbe, Martens, Olson & Bear

[57] ABSTRACT

A method for subtractive hybridization of desired DNA sequences from two cell or tissue populations. cDNA from experimental cells or tissues is modified by incorporation of nucleoside analogs to prevent subsequent exonuclease attack. Hybridization of the experimental and control cDNA is performed using the phenol-emulsion reassociation technique. The hybridized DNA is incubated with exonucleases, resulting in degradation of all but the desired duplex DNA which may then be amplified. This technique may be used to isolate differentially expressed genes or gene fragments and will contribute to our understanding of pathological conditions and developmental regulation.

18 Claims, 1 Drawing Sheet

PUBLICATIONS

Travis, et al., "Phenol Emulsion–Enhanced DNA–Driven Subtractive cDNA Cloning: Isolation of Low–Abundance Monkey Cortex–Specific mRNAs", *Proc. Natl. Acad. Sci. USA*, 85:1696–1700, 1988.

Wang, et al., "A Gene Expression Screen", *Proc. Natl. Acad. Sci. USA*, 88:11505–11509, 1991.

Wieland, et al., "A Method for Difference Cloning: Gene Amplification Following Subtractive Hybridization", *Proc. Natl. Acad. Sci. USA*, 87:2720–2724, 1990.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 21 base pairs
       ( B ) TYPE: nucleic acid
       ( C ) STRANDEDNESS: single

```
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

CTCTTGCTTG AATTCGGACT A                                             2 1

( 2 ) INFORMATION FOR SEQ ID NO:2:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

TAGTCCGAAT TCAAGCAAGA GCACA                                         2 5
```

ENZYMATIC DEGRADING SUBTRACTION HYBRIDIZATION

FIELD OF THE INVENTION

The present invention relates to the isolation of specific DNA sequences. More specifically, the invention relates to the rapid isolation of differentially expressed or developmentally regulated gene sequences through subtraction hybridization involving enzymatic degradation.

BACKGROUND OF THE INVENTION

The isolation of gene's whose expression differs between two cell or tissue types, or between cells or tissues exposed to chemical compounds or pathogens, is critical to understanding the mechanisms which underlie various physiological disorders. Changes in gene expression play a central role in many critical, therapeutically relevant processes including embryogenesis, aging, tissue repair and neoplastic transformation.

Several methods have been utilized for the detection and isolation of genes which are activated or repressed in response to developmental, physiological or pharmacological events. One of these methods, subtractive hybridization, is a particularly useful method for selectively cloning sequences present in one DNA population but absent in another. This selective cloning is accomplished by generating single stranded cDNA libraries from both control tissue (driver cDNA) and tissue during or after a specific change or response being studied (tester cDNA). The two cDNA libraries are denatured and hybridized to each other, resulting in duplex formation between the driver and tester cDNA strands if a particular sequence is common to both cDNA populations. Since the common sequences are removed, the remaining non-hybridized single-stranded DNA is enriched in sequences present in the experimental cell or tissue which is related to the particular change or event being studied (Davis et al., (1987) Cell, 51:987–1000).

Subtractive hybridization has led to the discovery of many important genes including the myogenesis differentiation marker MyoD1, the T-cell receptor and genes activated at the gastrulation stage of *Xenopus laevis* (Davis et al., 1987; Hedrick et al., (1984), Nature, 308:149–153; Sargent et al., (1983) Science, 222:135–139).

The power of the subtractive library method has been significantly enhanced by the polymerase chain reaction (PCR), which allows performance of multiple cycles of hybridization using small amounts of starting material (Wieland et al. (1990) *Proc. Natl. Acad. Sci. USA*, 87:2720–2724; Wang et al. (1991) *Proc. Natl. Acad. Sci. USA*, 88:11505–11509; Cecchini et al., (1993) *Nucleic Acids Res.*, 21:5742–5747).

PCR-driven subtraction hybridization using biotinylated control DNA has also been performed to identify differentially expressed genes (Lebeau et al., (1991) *Nucleic Acids Res.*, 19:4778; Duguid et al., (1990) *Nucleic Acids Res.*, 18:2789–2792). Duguid et al. ligated a duplex oligonucleotide referred to as an oligovector (also called a linker primer) to double stranded cDNA isolated from either control or scrapie-infected hamster brain, then digested the ligated DNA with a restriction enzyme to cleave the oligovector and reduce the amplification potential of the control DNA. The sequences were amplified by PCR and subtraction hybridization was performed to enrich for sequences present in infected brain, but absent in uninfected brain. DNA isolated from normal brain was biotinylated, mixed with DNA from infected brain, denatured and hybridized to normal DNA, and biotinylated complexes were removed. The subtracted DNA was then subjected to further subtraction/amplification cycles.

There are a number of problems associated with the existing PCR-directed subtraction hybridization methods. First, preventing amplification of the control cDNA by restriction enzyme digestion of its linker primer is often inefficient and unreliable (Kaufman et al., (1990) *Biotechniques*, 9:304–306). Second, since the biotinylation reaction does not proceed to completion, the subtracted cDNA is often contaminated with control cDNA which is present in the initial hybridization mixture in large excess. Moreover, the method for separating biotinylated and unbiotinylated molecules is tedious and large amounts of cDNA and expensive reagents are required. In addition, the contamination by control cDNA may necessitate an additional screening step prior to the final selection of differentially expressed genes.

There is a need for a rapid, low cost, simple, reliable, reproducible, PCR-directed subtraction hybridization method for identification of clinically and therapeutically relevant differentially expressed genes which will overcome the inherent problems associated with the prior art methods. The present invention provides such a method.

SUMMARY OF THE INVENTION

One embodiment of the present invention is a method for performing subtractive cDNA hybridization, including some or all of the following steps:

(a) providing a library of tester cDNA which is protected from digestion by a first nuclease;

(b) contacting the tester cDNA in denatured form with a library of denatured driver cDNA which is unprotected from digestion by the first nuclease, to form a denatured mixture;

(c) permitting cDNA in the denatured mixture to form double stranded cDNA comprising homo- and heteroduplexes;

(d) digesting unprotected cDNA with the first nuclease; and (e) treating the resulting material with a second nuclease to digest single stranded cDNA and thereby provide a library enriched in tester cDNA that is not present in the library of driver cDNA.

In one aspect of this embodiment, steps (b)–(e) are repeated on the enriched library at least one time. In another aspect of this preferred embodiment, the enriched library is amplified. Preferably, this amplification is by PCR. Advantageously, the tester cDNA is protected from digestion by the first nuclease by incorporating therein exonuclease-resistant nucleotide analogs. Preferably, the analogs are deoxynucleoside thiotriphosphates. According to another aspect of this embodiment, the nucleotide analogs are incorporated into the tester cDNA by DNA polymerase. Preferably, the DNA polymerase is the Klenow enzyme. This embodiment also provides that the homo- and heteroduplexes are formed by the phenol-emulsion reassociation technique. Advantageously, the first and second nucleases are exonucleases III and VII, respectively. Preferably, the driver cDNA and tester cDNA have a ratio of between about 10:1 and about 50:1; most preferably, the ratio is about 20:1.

The present invention also includes a kit for performing subtractive cDNA hybridization, comprising:

(a) deoxynucleoside triphosphate analogs which confer resistance to exonuclease digestion upon incorporation into a DNA molecule;

(b) a combined 3' to 5' exonuclease activity and 5' to 3' polymerase activity;

(c) a double strand-specific 3' exonuclease;

(d) 3' exonuclease buffer; and (e) a single strand-specific exonuclease Preferably, the analogs are deoxynucleoside thiotriphosphates and the enzymatic activity in (b) is the Klenow enzyme. Advantageously, the double strand-specific 3' exonuclease is exonuclease III and the single strand-specific exonuclease is exonuclease VII.

DETAILED DESCRIPTION OF THE INVENTION

Figure 1:
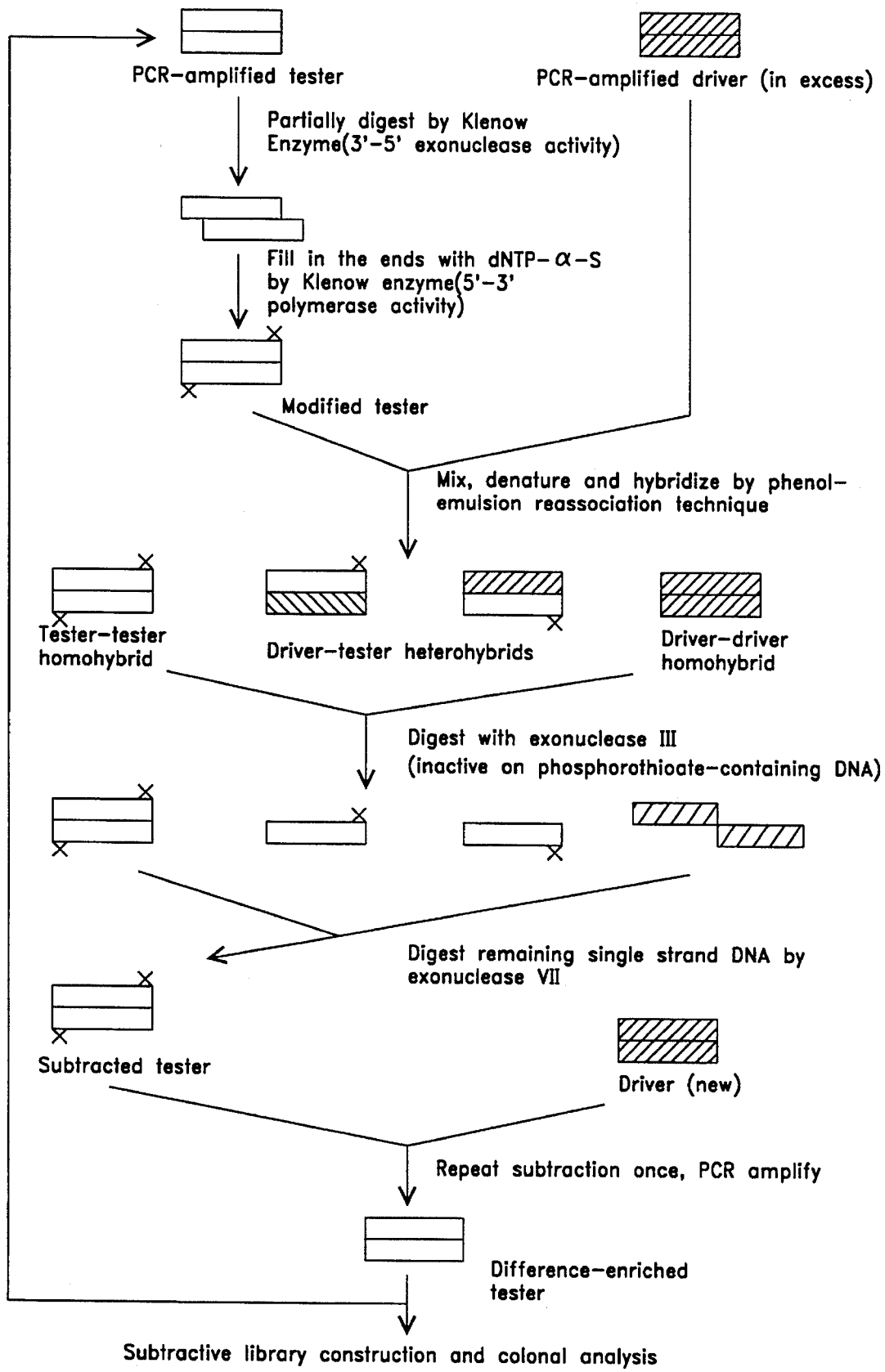
FIG. 1 is a schematic diagram illustrating the enzymatic degrading subtraction technique. The preparation of tester and driver cDNA fragments by digestion with restriction endonuclease and PCR amplification after ligation with a linker-primer is described in Example 2 below.

The present invention provides an alternative method for differential cDNA library construction and gene cloning called enzymatic degrading subtraction (EDS). This method is primarily designed for detecting differentially expressed genes (either up- or down-regulated) and employs rapid, simple enzymatic manipulations for inhibiting exonuclease degradation of the DNA of interest, and also for removing sequences common to both cells or tissues as well as undesirable DNA sequences from control tissue. The phenol-emulsion reassociation technique (PERT) (Kohne et al., (1977) *Biochemistry*, 16:5329–5341; Travis et al., (1988) *Proc. Natl. Acad. Sci. USA*, 85:1696–1700), used in conjunction with this method, allows the cDNA molecules to be efficiently subtracted using a very small amount of DNA as this technique significantly accelerates the hybridization rate.

As used herein, tester DNA refers to DNA isolated from cells or tissues which are stimulated, differentiated, exposed to a chemical compound or are infected with a pathogen (the experimental cells or tissues). It is the desirable tester DNA which is subtracted out from the total DNA population, leaving the degraded driver DNA behind. The tester DNA contains the sequences of interest which are either up- or down-regulated in response to a particular condition. Driver DNA refers to DNA isolated from unstimulated or undifferentiated cells or tissues (i.e., "normal" or control cells or tissues). The driver DNA is used to completely remove sequences common to driver and tester cDNA populations through hybridization and subsequent exonuclease digestion, thus substantially enriching for sequences present in only the tester DNA. cDNA sequences which are subtracted out are referred to herein as selectively expressed, differentially expressed, enriched or difference-enriched sequences.

cDNA fragments of less than 1 kilobase are prepared by restriction enzyme digestion and linker ligation according to Wang and Brown (*Proc. Natl. Acad. Sci. USA*, 88:11505–11509, 1991). The cDNA fragments are then amplified using PCR. In a preferred embodiment, referring to FIG. 1, the 3' ends of the tester cDNA are labelled with phosphorothioate nucleotide analogs (dNTP-α-S) to prevent their subsequent degradation by exonucleases. Although dNTP-α-S analogs were used to block the 3' ends of the tester cDNA, any nucleotide analog capable of being incorporated into the tester cDNA and protecting it from nuclease attack is within the scope of the present invention. The existing 3' ends are partially digested using the large fragment of DNA polymerase I (Klenow enzyme) which possesses a 3' to 5' exonuclease activity, followed by addition of deoxynucleoside thiotriphosphates to fill in the ends of the molecule and to protect the modified duplex from digestion with exonucleases. This filling-in reaction is also performed by the Klenow enzyme which possesses a 5' to 3' DNA polymerase activity as well as a 3' to 5' exonuclease activity.

In another preferred embodiment, the modified tester cDNA is then mixed with an excess of driver DNA, denatured and hybridized using the PERT technique. It is preferred that the ratio of driver to tester DNA be in the range of about 5:1 to about 100:1. In a most preferred embodiment, the ratio is between 10:1 and 50:1. If the ratio of driver to tester cDNA is too high, successful enrichment will not be obtained for genes which are only up- or down-regulated several fold. If the ratio of driver to tester cDNA is too low, sequences common to both driver and tester will be present in the subtracted library and will not have been effectively selected out. Therefore, more rounds of subtraction will be required to remove the common sequences. The optimal ratio of driver to tester cDNA for cloning a particular gene will vary depending on the level of up- or down-regulation. This ratio can be determined by routine experimentation using the protocols described hereinbelow.

During the hybridization step, tester DNAs which self-hybridize will contain the phosphorothioate nucleotides at both 3' ends, whereas tester-driver heteroduplexes will only have one 3'-modified end since the driver DNA is unmodified (FIG. 1). In another preferred embodiment, incubation with exonuclease III, an enzyme which rapidly and synchronously degrades double stranded DNA from the 3' ends, results in hydrolysis of the driver-tester and driver-driver hybrids to form single strands, while the 3'-protected tester-tester duplex remains intact. Incubation with other double strand-specific 3' exonucleases is also contemplated.

Alternatively, the thionucleotide analogs may be incorporated into the tester cDNA at the 5' end by incorporation into the PCR primer prior to the initial PCR amplification. In this case, a 5'-specific exonuclease such as the phage T7 gene 6 protein will degrade the unprotected double stranded DNA from its 5' ends to produce single strands, resulting in intact tester-tester duplexes.

In still another preferred embodiment, the exonuclease III-treated DNA hybrids are incubated with exonuclease VII, a single strand-specific exonuclease which degrades DNA from both the 5' and 3' ends. This results in complete degradation of the tester and driver single DNA strands to mono- and oligonucleotides, leaving the tester-tester cDNA homoduplex intact. Incubation with any other single strand-specific exonuclease capable of degrading the remaining tester and driver cDNA is also within the scope of the present invention. Such contemplated exonucleases for use in this step include mung bean nuclease and S1 nuclease (Pharmacia LKB, Piscataway, N.J.).

The subtracted tester cDNA is then subjected to another round of subtraction and amplified by PCR. The amplified sequences are used for cDNA library selection and clonal analysis and represent DNA sequences present only in stimulated, differentiated or treated cells. Since the incubation of driver cDNA with exonuclease III destroys the amplification potential of the driver cDNA, this ensures that only the subtracted tester cDNA is later amplified and exponentially enriched by PCR. The amplified PCR fragments can then be used to probe a standard cDNA library constructed from tester cDNA to obtain inserts containing complete open reading frames. The corresponding protein sequences may be determined and used to search protein databases to establish similarity or identity to any known protein.

The present invention will be useful in the identification of differentially expressed genes and rearranged gene fragments involved in embryonic development and in the onset or maintenance of various pathological conditions, including cancer, neurodegenerative disorders, autoimmune diseases, and any other disorder caused in whole or in part to differential gene expression. The identification of these genes and gene fragments and their corresponding polypeptides will contribute to the understanding of the pathogenesis of these conditions. Most importantly, this understanding will enable the development of therapeutics for treatment of these disorders. Such therapeutics include small molecule enzyme inhibitors, monoclonal antibodies, antisense RNA, ribozymes and any other therapeutic method capable of regulating the activity of the selectively expressed DNA, mRNA or protein product of interest.

The method of the present invention may also be used to determine the contribution of increased or decreased gene expression to various birth defects during fetal development. Once candidate genes are identified, treatments may be developed to prevent the development of these defects by regulating expression of the corresponding genes or the function of the expressed proteins contributing to these developmental abnormalities.

Although EDS is primarily designed for isolating genes whose expressions differ between two types of cells or tissues, the method will also be useful in the determination of small differences between two complex genomes arising as a result of genetic alterations such as programmed gene rearrangements of DNA in somatic cells during carcinogenesis and tumorigenesis. Representational difference analysis (RDA) has recently been developed for the purification of restriction fragments present in one DNA population but absent in another by subtractive and kinetic enrichment (Lisytsin et al., (1993) *Science*, 259:946–951). In RDA, the targets are purified by PCR using different pairs of primers after each step of enrichment. The cost of making multiple sets of oligonucleotides as well as the time consuming process required to remove old primers and religate new primers represents significant problems associated with the method. Thus, EDS may be incorporated into RDA for the isolation of probes for these genomic rearrangements. The identification of such rearrangements will be useful as a diagnostic indicator of transformed cells or of the potential for neoplastic transformation.

The present invention may also be provided in the form of a kit containing the necessary primers, enzymes, buffers and nucleotide analogs. The kit will enable the subtractive cloning of selectively expressed genes from desired cells or tissues in a rapid, convenient, reliable manner.

The modification of tester DNA prior to subtraction confers several important advantages. First, modification with dNTP-α-S is much more efficient and much less expensive than restriction digestion of driver cDNA followed by biotinylation. Labeling with dNTP-α-S avoids the use of large quantities of costly reagents and enzymes as well as specialized devices necessary for the biotin photoactivation reaction. Moreover, the present method requires only a single fast preparative step prior to hybridization in contrast to the several time-consuming steps used in previous methods. Most importantly, the Klenow enzyme-mediated modification of tester cDNA can be carried out in a controlled uniform manner due to its slow and synchronous excision activity and relatively highly processive polymerase activity. Thus, each tester cDNA is labeled with the thionucleotide derivatives to the same degree by the polymerase. In contrast, incorporation of biotin into driver cDNA by photoreaction is inefficient and requires repeated reaction to increase the density of labeling (Wang et al., (1991) *Proc. Natl. Acad. Sci. USA*, 88:11505–11509).

An additional benefit of such a tester modification is that the PERT technique which greatly enhances the hybridization rate can be incorporated into PCR-driven subtractive hybridization. The PERT technique greatly reduces the total amount of DNA necessary for hybridization (only several micrograms) due to its ability to accelerate the reassociation rate up to a maximum of about 25,000 fold. This is particularly important when mRNA is obtained from a source having limited availability. PERT also facilitates obtaining cDNAs corresponding to rare mRNAs which may function as important regulatory molecules. In contrast, the previous subtraction methods employing the biotinylated driver are not amenable to PERT since the modified DNA is partitioned into the organic phenol phase and forms an insoluble precipitate.

Thus, EDS is a rapid, cost-effective, reliable method for construction of a subtracted cDNA library. By enzymatically degrading the common and driver cDNAs, EDS bypasses labor-intensive physical or chemical separation which requires chromatography and organic solvent extraction, thus minimizing both time and handling of the reaction mixture. The use of EDS enables isolation of selectively expressed cDNAs in about two weeks, including isolation of mRNA, synthesis of cDNA and subtraction hybridization, compared to the approximately two month period required using traditional subtraction techniques (Liang et al., (1992) *Science*, 257:967–971).

The performance of each step in EDS is controlled since the enzymes are extremely specific and reliable. The high efficiency of this procedure is illustrated by the fact that several differentially expressed cDNA fragments from adult rat brain were already visible after the first round of hybridization (see Example 5). The sequence enrichment was essentially complete after a second round of subtraction as evidenced by agarose gel analysis of the PCR amplified cDNA fragments (see Example 5) and by the library screening results (see Example 7).

A comparative hybridization using a duplicate lift technique is an absolute requirement for the final isolation of selectively expressed genes in most previous PCR-driven subtraction protocols and frequently in a newly developed differential display technique (Liang et al., (1992) *Science*, 257:967–971). This technique has a high false-positive rate (Liang et al., (1993) *Nucleic Acids Res.*, 21:3269–3275), thus labor-intensive screening is needed to sort out the selectively expressed genes by testing a large number of candidate clones. This step is eliminated by EDS as demonstrated herein in the successful construction of a subtractive library for adult rat brain specific mRNAs.

cDNA was prepared from embryonic and adult rat brains as described below.

EXAMPLE 1 cDNA preparation

Pregnant Sprague-Dawley rats were sacrificed in a sealed $CO_2$ chamber. Embryonic day 19 rat fetuses were surgically removed from the uteri and anesthetized in ice. The brains were quickly removed, frozen on dry ice and stored at −80° C. Adult rat brains were purchased from BPS, Inc. (Indianapolis, Ind.). Total RNA was isolated from embryonic and adult rat brains by the acid guanidinium isothiocyanate single-step method (Chomczynski et al., (1987) *Anal. Biochem.*, 162:156–159) using a kit (5 prime to 3 prime, Boulder, Colo.). Poly(A)$^+$ RNA was isolated by oligo(dT) cellose column chromatography (PolyA quick; Stratagene, La Jolla, Calif.) and treated with DNase I. Oligo(dT)-primed (Gibco BRL, Gaithersburg, Md.) first strand cDNA synthesis was performed using 7 μg poly(A)$^+$ RNA and reverse transcriptase. The second cDNA strand was synthesized according to the manufacturer's protocol by methods well known in the art of molecular biology (Sambrook et al., (1989) *Molecular Cloning: A Laboratory Manual*, Cold Spring Harbor Laboratory Press, Cold Spring harbor, N.Y.).

cDNA fragments were prepared and amplified as described in the following example.

EXAMPLE 2

Digestion Linker Ligation and PCR Amplification

The preparation of cDNA fragments by restriction enzyme digestion and linker ligation was carried out essentially according to Wang and Brown (1991). Aliquots of cDNA were digested with either AluI or AluI+RsaI (Gibco BRL), restriction enzymes which recognize 4 base pair sequences and cut often, resulting in DNA fragments less than 1 kilobase in length. Oligodeoxynucleotides having a flush end (5'-CTCTTGCTTGAATTCGGACTA-3'; SEQ ID NO: 1) and a 4 base 3' protruding end (5'- TAGTCCGAATTCAAGCAAGAGCACA-3'; SEQ ID NO:2) (Duguid et al., (1990) *Nucleic Acids Res.*, 18:2789–2792) were prepared by conventional methods using an automated DNA synthesizer. The oligonucleotides were phosphorylated using T4 polynucleotide kinase (New England Biolabs, Beverly, Mass.) and hybridized in T4 kinase buffer (70 mM Tris-HCl, pH 7.6, 10 mM MgCl$_2$5, mM DTT) yielding a duplex linker.

The linker was ligated separately to the blunt end of the adult and embryonic rat brain cDNA restriction fragments using T4 DNA ligase (New England Biolabs). Unligated linkers were removed by centrifugation through a Centricon-50 membrane (Amicon, Beverly, Mass.) and ligated cDNA fragments were collected into 1 ml of distilled deionized water. Ten μl of the cDNA solution was amplified in a 100 μl PCR reaction containing 1.5 mM MgCl$_2$, 1 μg primer (SEQ ID NO:1), 5 units Taq polymerase (Gibco BRL), 200 μM dNTPs (94° C., 1 min.; 52° C., 1 min.; 72° C., 2 min.; 30 cycles). Two and six such PCRs were performed for the tester (adult brain) and driver (embryonic brain) eDNA fragments, respectively. The amplified cDNAs were desalted by centrifugation through a Centricon-50 or by ethanol precipitation.

Phosphorothioate nucleotides were incorporated into the 3' ends of the tester cDNA as described below.

EXAMPLE 3

Incorporation of Phosphorothioate Nucleotides

Five μg of PCR-amplified tester cDNA fragments were incubated with 50 units Klenow enzyme (New England Biolabs) in a volume of 100 μl for 45 min. at 37° C. The reaction mixture was then supplemented with 10 μl 0.4 mM deoxynucleotide thiotriphosphates (Pharmacia LKB) and incubated for 30 minutes. The sample was then phenol-chloroform extracted and desalted using Centricon-50 centrifugation or ethanol precipitation.

The 3'-modified tester cDNA fragments were hybridized with unmodified driver cDNA fragments as described in the following example.

EXAMPLE 4

Phenol emulsion-enhanced reassociation

Modified tester cDNA fragments (0.25 μg) were combined with an excess of driver cDNA fragments (5 μg) in 120 μl 40 mM Tris-HCl, pH 8.0, 4 mM EDTA. The sample was denatured by heating for 5 min at 95° C. Hybridization was performed using the PERT technique in 500 μl 2 M sodium thiocyanate, 8% phenol at room temperature for 20–24 hours. The emulsion was maintained by continuous agitation on a vortex mixer (Eppendorf). After hybridization, the solution was extracted with chloroform and desalted by centrifugation through a Centricon-50 or ethanol precipitated.

Enzymatic degradation of the hybridized DNA was performed as described below.

EXAMPLE 5

Enzymatic Degradation of hybridized DNA

The reaction mixture from Example 4 was incubated with 100 units of *E. coli* exonuclease III (United States Biochemical Corp., Cleveland, Ohio) in 200 μl 50 mM Tris-HCl, pH 8.0, 5 mM MgCl$_2$, 10 mM 2-mercaptoethanol for 8–10 min. at 37° C. The reaction mixture also contained a trace amount of the Klenow enzyme (5 units) to excise 3' ends of originally ligated driver cDNA molecules used as a template for PCR amplification since exonuclease III cannot efficiently degrade duplexes having 3' protruding ends of more than 4 bases. Alternatively, if a linker having a 5' end is chosen, the use of Klenow enzyme can be omitted since 5' protruding ends are good exonuclease III substrates.

After addition of 3 μl 0.5 M EDTA and 20 μl 0.5 M potassium phosphate, pH 7.6, the reaction mixture was supplemented with 20 units exonuclease VII (United States Biochemical Corp.). and incubated for at least 30 min. to allow degradation of single stranded DNA. The sample was extracted once with phenol/chloroform, once with chloroform and desalted by Centricon-50 or ethanol precipitation. The resulting subtracted cDNA was again hybridized to 5 μg driver cDNA. This is termed one cycle of subtraction. The enriched subtracted cDNAs after each successive cycle of subtraction were amplified by 20, 15 and 15 cycles of PCR, respectively, using the same parameters descried above. A total of three cycles of subtraction were performed. Only 0.125 μg tester DNA was included in the last cycle of subtraction.

The subtractive process was monitored by agarose gel electrophoresis of PCR amplified cDNA fragments from each round of subtraction. The original unsubtracted cDNAs from adult rat brain moved as a smear between 0.15 and 0.7 kb. Interestingly, several distinct bands were present between 0.2 and 0.4 kb after the first cycle of subtraction. The intensities of these bands gradually increased with successive subtractions due to the continual removal of sequences common to both tester and driver cDNA. The enrichment process was essentially complete after the second cycle of subtraction. These DNA species represented the enriched subtracted cDNA sequences and corresponded to the differentially expressed mRNAs in adult rat brain.

Although three cycles were performed, it can be appreciated that any number of cycles may be performed depending on the specific reaction conditions, sequence abundance and driver cDNA to tester cDNA ratio.

Resistance of double stranded tester cDNA to hydrolysis by exonuclease III after 3' end labeling with deoxynucleotide thiotriphosphates was assessed as described below.

EXAMPLE 6

Resistance of modified tester DNA to exonuclease III

Modified and native cDNAs were tested to determine their susceptibility to digestion by exonuclease III. Unmodified cDNA fragments from adult male rat brain were completely degraded to single strand DNAs after a short incubation with exonuclease III as determined by electrophoresis on a 2% agarose gel followed by staining with ethidium bromide. In contrast, the cDNA fragments having 3' ends modified with the thiotriphosphates remained intact after incubation with the exonuclease.

The subtracted library was constructed as described below.

EXAMPLE 7

Construction and PCR analysis of Subtracted Library

PCR amplified products from Example 5 were directly ligated into the PCR II prokaryotic expression vector (Invitrogen, San Diego, Calif.) and used to transform competent INVαF' cells (Invitrogen) following the procedures of the TA cloning kit (Invitrogen). Approximately 3,000 recombinant-containing colonies were obtained. For clonal analyses, white colonies (containing inserts) were randomly picked and placed in 50 μl water. The colonies were heated for 10 min. at 100° C., centrifuged, and the supernatants containing the inserts were amplified by PCR (94° C, 1 min.; 56° C., 50 sec.; 72° C., 50 sec.; 20 cycles) using the linker primer (SEQ ID NO:1). Of the initial 16 colonies screened, 11 contained inserts representing selectively expressed mRNAs.

Northern blot analysis was then performed to demonstrate that successful differential gene expression by EDS had occurred.

EXAMPLE 8

Northern Blot Hybridization

Total RNA (5 μg) isolated from both embryonic and adult rat brains was separated by electrophoresis through a 1.2% agarose-formaldehyde gel and transferred to a nylon filter (Genescreen Plus; New England Nuclear, Boston, Mass.). The filters were baked under vacuum at −80° C. for several hours. DNA probes from two PCR-amplified inserts (probes a1 and a4) were prepared using a random-prime labeling kit (Boehringer Mannheim, Indianapolis, Ind.) in the presence of α-[$^{32}$P]dCTP and had specific activities of approximately $1\times10^7$ cpm/ml. Northern blot hybridization was carried out for 16–18 hours at 45° C. in Hybrisol I solution (Oncor, Gaithersburg, Md.). Blots were rinsed briefly with 2×SSPE, 0.1% SDS at room temperature followed by a 30 min. wash in 0.1×SSPE, 0.1% SDS at 65° C.

Two specific mRNAs of approximately 2.5 kilobases and 0.9 kilobases were detected in adult but not embryonic rat brains by probes a1 and a4, respectively. Although the two probes were similar in length and had the same specific activity, a large difference in signal intensity was observed after the exposure of the two blots to x-ray film for a similar time, indicating a very different abundance of the two messages in adult rat brain. The mRNAs probed by a1 and a4 appeared to be present in low and moderate abundance in the tissue, respectively. These results indicate the utility of EDS for the identification of specific mRNAs of vastly different concentrations.

EXAMPLE 9

Differential Expression of Genes in Tumor Cells

Tumors are induced in mice by injection of transformed 3T3 fibroblasts. The mice are sacrificed and both tumor and normal tissue is isolated. cDNA is prepared from the tumor (tester) and normal tissue (driver) using well known methods (see i.e., Sambrook et al., (1989), *Molecular Cloning: A Laboratory Manual,* Cold Spring Harbor Laboratory Press, Cold Spring Harbor, N.Y.). The cDNAs are digested with AluI, ligated to the linker primer and PCR amplified as described in Example 2. The subtractive hybridization method described in Examples 3–5 is then performed followed by a second round of subtraction hybridization. The resulting subtracted tester cDNA is amplified, inserted into a prokaryotic expression vector and used to transform competent cells. These inserts are isolated, random-prime labeled and used to probe a Northern blot of RNA isolated from both normal and tumor tissue. A signal is observed only on the blot containing the tumor RNA.

The present invention has been described with reference to particular preferred embodiments; however, the scope of the invention is defined by the attached claims and should be construed to include reasonable equivalents.

---

What is claimed is:

1. A method of performing subtractive cDNA hybridization to obtain a first library enriched in cDNA that is not present in a second library, comprising the steps of:
   (a) providing a library of tester cDNA, wherein said tester cDNA is protected from digestion by a first nuclease;
   (b) contacting said tester cDNA in denatured form with a library of denatured driver cDNA, wherein said driver cDNA is not protected from digestion by said first nuclease, to form a denatured mixture;
   (c) permitting cDNA in said denatured mixture to form double stranded cDNA comprising homo- and heteroduplexes;
   (d) digesting unprotected cDNA with said first nuclease; and
   (e) treating the resulting material with a second nuclease to digest single stranded cDNA and thereby provide a library enriched in tester cDNA that is not present in said library of driver cDNA.

2. The method of claim 1, further comprising repeating steps (b)–(e) on said enriched library at least one time.

3. The method of claim 2, further comprising amplifying said enriched library.

4. The method of claim 3, wherein said amplification is PCR amplification.

5. The method of claim 1, wherein said tester cDNA is protected from digestion by said first nuclease by incorporating therein exonuclease-resistant nucleotide analogs.

6. The method of claim 5, wherein said nucleotide analogs are deoxynucleoside thiotriphosphates.

7. The method of claim 6, wherein said nucleotide analogs are incorporated into said tester cDNA by DNA polymerase.

8. The method of claim 7, wherein said DNA polymerase is Klenow enzyme.

9. The method of claim 1, wherein said homo- and heteroduplexes are formed by the phenol-emulsion reassociation technique.

10. The method of claim 1, wherein said first nuclease is exonuclease III.

11. The method of claim 1, wherein said second nuclease is exonuclease VII.

12. The method of claim 1, wherein said driver cDNA and said tester cDNA have a ratio of between about 10:1 and about 50:1.

13. The method of claim 12, wherein said ratio is about 20:1.

14. A kit for performing subtractive cDNA hybridization, comprising:
   (a) deoxynucleoside triphosphate analogs; wherein said analogs confer resistance to exonuclease digestion upon incorporation into a DNA molecule;
   (b) a combined 3' to 5' exonuclease activity and polymerase activity;
   (c) a double strand-specific 3' exonuclease;
   (d) 3' exonuclease buffer; and
   (e) a single strand-specific exonuclease.

15. The kit of claim 14, wherein said analogs are deoxynucleoside thiotriphosphates.

16. The kit of claim 14, wherein said combined activity recited in (b) is the Klenow enzyme.

17. The kit of claim 14, wherein said double strand-specific 3' exonuclease is exonuclease III.

18. The kit of claim 14, wherein said single strand-specific exonuclease is exonuclease VII.

* * * * *